(12) United States Patent
Maass et al.

(10) Patent No.: US 6,793,825 B2
(45) Date of Patent: Sep. 21, 2004

(54) PROCESS FOR THE SEPARATION OF ORGANIC SUBSTANCES FROM AN AQUEOUS MIXTURE

(75) Inventors: Dietrich H. Maass, Altenberge-Hansell (DE); Dirk Weuster-Botz, Dachau (DE); Ralf Takors, Merzenich (DE); Christian Wandrey, Jülich (DE); Holger Paschold, Linnich (DE)

(73) Assignee: DSM IP Assets B.V., Heerlen (NL)

( * ) Notice: Subject to any disclaimer, the term of this patent is extended or adjusted under 35 U.S.C. 154(b) by 261 days.

(21) Appl. No.: 09/984,290

(22) Filed: Oct. 29, 2001

(65) Prior Publication Data

US 2002/0158020 A1 Oct. 31, 2002

Related U.S. Application Data

(63) Continuation-in-part of application No. PCT/EP00/03705, filed on Apr. 26, 2000.

(30) Foreign Application Priority Data

Apr. 29, 1999 (DE) .......................................... 199 19 490

(51) Int. Cl.⁷ ................................................ C02F 1/44
(52) U.S. Cl. ....................... 210/644; 210/641; 210/639; 426/23; 562/11; 435/139
(58) Field of Search ................................ 210/634, 639, 210/644, 648, 641; 426/43; 562/11, 554; 435/139

(56) References Cited

U.S. PATENT DOCUMENTS

| | | | | |
|---|---|---|---|---|
| 3,454,490 A | * | 7/1969 | Wallace ....................... 210/638 |
| 4,411,991 A | * | 10/1983 | Hirakawa et al. ............. 435/42 |
| 5,153,355 A | * | 10/1992 | Mildenberger et al. ........ 562/11 |
| 5,350,681 A | * | 9/1994 | Iacobucci et al. ........... 435/68.1 |
| 5,681,728 A | * | 10/1997 | Miao ........................... 435/136 |
| 6,171,501 B1 | * | 1/2001 | Eyal et al. ................... 210/634 |
| 6,433,163 B1 | * | 8/2002 | Ho .............................. 540/315 |
| 6,534,679 B2 | * | 3/2003 | Eyal et al. ................... 562/589 |

FOREIGN PATENT DOCUMENTS

| | | | |
|---|---|---|---|
| EP | 0250666 | * | 1/1988 |
| WO | WO 00/66253 | * | 9/2000 |

* cited by examiner

*Primary Examiner*—Ana Fortuna
(74) *Attorney, Agent, or Firm*—Meyer, Brown, Rowe & Maw LLP

(57) ABSTRACT

The present invention relates to a process for separating from an aqueous mixture one or more organic substances containing at least one positively charged and/or chargeable nitrogenous group by means of extraction via at least one porous membrane, wherein use is made of an extraction agent which contains at least partially relatively long-chain organic compounds and at least one liquid cation exchanger, and of a membrane that is wettable by either the aqueous mixture or by the extraction agent. In particular, the invention relates to a process for separating from an aqueous mixture one or more organic substances containing at least one positively charged and/or chargeable nitrogenous group by means of extraction via at least one porous membrane, wherein the aqueous mixture is drawn from a reservoir 1, led across a first porous membrane 3 which is wettable by either the aqueous mixture or by an extraction agent 5 which contains at least partially relatively long-chain organic compounds and at least one liquid cation exchanger, extracted with the extraction agent 5, the aqueous retentate is returned to the reservoir, the extracted organic substances are led across a second porous membrane 6 which is wettable by either the aqueous mixture or by the extraction agent and there re-extracted into an aqueous phase 7.

20 Claims, 1 Drawing Sheet

PROCESS FOR THE SEPARATION OF ORGANIC SUBSTANCES FROM AN AQUEOUS MIXTURE

Figure 1:
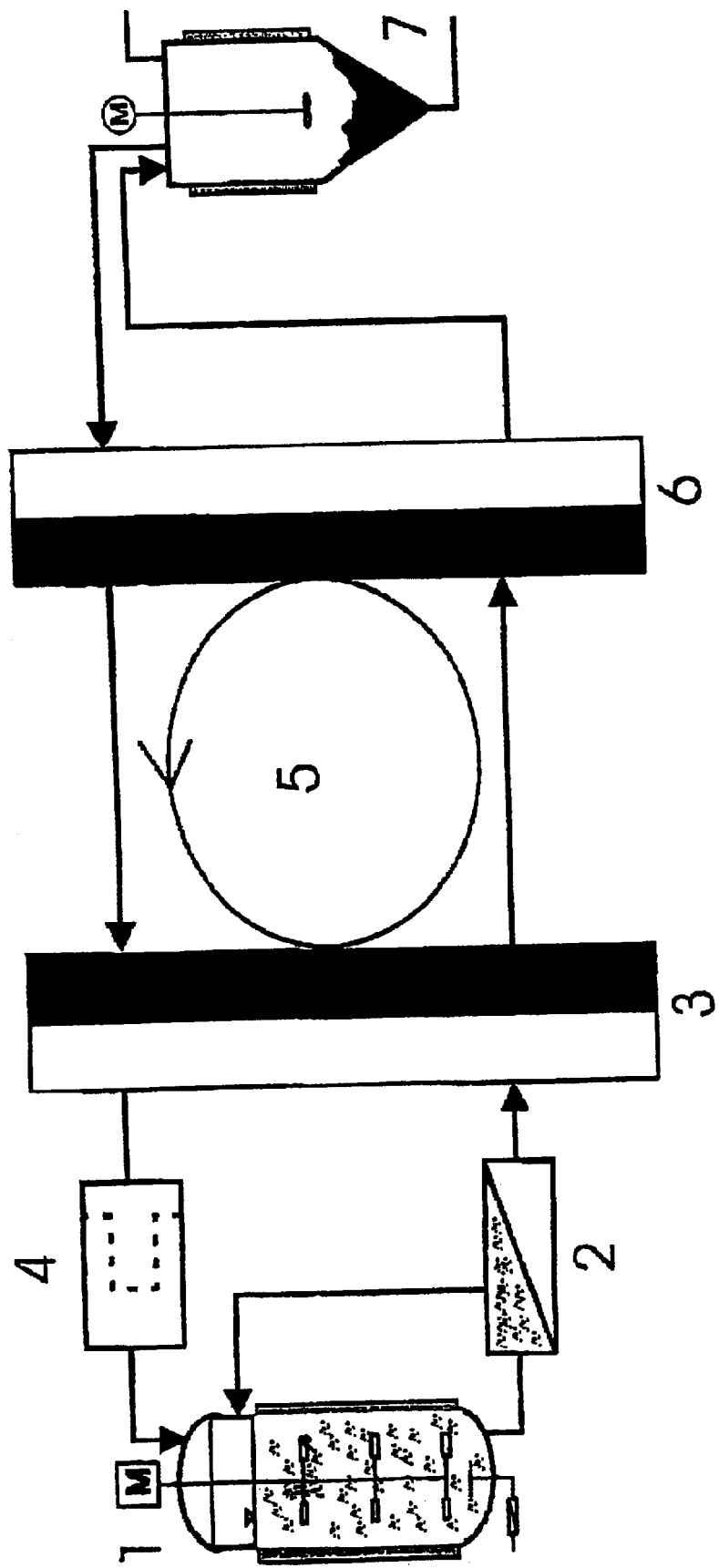

This is a Continuation-In-Part of International application Serial No. PCT/EP00/03705 filed Apr. 26, 2002, which designated the U.S. and was published in English.

The present invention relates to a process for separating from an aqueous mixture one or more organic substances containing at least one positively charged and/or chargeable nitrogenous group by means of extraction via at least one porous membrane.

Numerous techniques for the separation of organic compounds from aqueous solutions are known, such as separation via ion exchange resins, chromatography processes, adsorption, filtration, evaporation, reverse osmosis, electrodialysis, etc.

In this relation the recovery of amino acids in particular has gained in economic interest in recent years, in the first place in connection with the foodstuffs and beverages industries. Separation of the required amino acids from mixtures is effected for instance in particular via ion exchangers or for instance by means of reactive extraction. Where purification of especially culture broths is concerned, limitations are encountered with these processes however. When culture liquids are treated by means of ion exchangers it is a drawback that the mixture to be treated requires an extensive pretreatment.

For the purification of in particular L-phenylalanine extraction processes involving several liquid membranes have been described (Thien, M. P. et al., Biotechnol Bioeng, 1998, 32: 604–615). In the widest sense this relates to oil-in-water emulsions with formation of organic, for instance lipids-containing, membrane vesicles, through which the actual extraction then takes place. However, at high product concentrations such liquid-liquid extraction processes are subject to limitations due to considerable swelling of the membrane vesicles. In addition, the stability of the membrane vesicles is pressure sensitive.

Dispersion-free extraction processes via hollow fibres for separation of L-phenylalanine are already known from Escalante H. et al. (1998, Separation Science and Technology, 33(1): 119–139). The extraction agent used in this case is a mixture of quaternary ammonium salts, isodecanol and kerosine, which, it should be noted, exhibits a strong selectivity towards anions. The drawback of this process is that the extraction of L-phenylalanine requires a titration of the medium at a pH value of 10.5. The re-extraction from the organic phase requires another titration at a pH value of 0.5. In addition, because of the toxicity of the extraction agent, in particular the quaternary ammonium salts, which are also used as disinfectants, direct recycling of the medium into the production process is not possible. An additional drawback of this process lies in the circumstance that separation of the L-phenylalanine cannot be integrated with the fermentation process, so that it is not possible to prevent a potential product inhibition.

The extraction of amino acids via a cation-selective extraction agent consisting of di-2-ethylhexylphosphoric acid dissolved in n-decanol has been described by Teramoto M. et al (1991, J. Membr. Sci. However, this involves a liquid-membrane system, presenting the drawbacks mentioned in the foregoing, especially in respect of the low stability of the liquid membrane vesicles. A further drawback is that the components of the extraction agent used are toxic to biological production systems, e.g. fermentation systems, which means that the scope of application of this process is restricted to batch extraction. Also in this case therefore it is not possible to make use of an integrated separation system in order to prevent a potential product inhibition.

Wieczorek S. et al. (1998, Bioprocess Engineering, 18: 75–77) describes the use of a mixture of tridodecylamine, kerosine and octanol as extraction agent. This process is not aimed at recovery of amino acids, as in the case of the systems referred to above, but at separation of citric acid, a nitrogen-free substance, from the culture broth of the fungus *Aspergillus niger* by means of an anion-selective carrier. Also in the case of this system, the high toxicity of the extraction agent is a drawback. That is why returning of the medium to the production process requires the introduction of additional, costly process or, more specifically, purification steps, as a consequence of which, moreover, only partial recycling of the medium can be achieved.

The aim of the present invention therefore is to provide a process for separating from an aqueous mixture one or more organic substances containing at least one positively charged and/or chargeable nitrogenous group by means of extraction via at least one porous membrane, which process does not present the above-mentioned drawbacks.

This aim is accomplished due to the use of an extraction agent which contains at least partially relatively long-chain organic compounds and at least one liquid cation exchanger, and of a membrane that is wettable by either the aqueous mixture or by the extraction agent.

The liquid cation exchanger serves as a carrier. According to the invention the organic substances are preferably re-extracted from the extraction agent into an aqueous phase.

The relatively long-chain compounds used preferably are compounds which are poorly miscible with or poorly soluble in water and are liquid at temperatures between 10 and 60° C., preferably between 20 and 40° C. Compounds with 6 to 20 C. atoms are preferred according to the invention; particular preference is given to compounds with 12 to 18 C. atoms. Such compounds may be branched, non-branched, saturated, non-saturated or partially aromatic organic compounds. Examples of relatively long-chain organic compounds according to the invention are alkanes, alkenes or fatty acid esters or mixtures of several of these compounds. These compounds serve as solvents in the process according to the invention.

Alkanes to be used are for instance hexane, cyclohexane, decane, ethyl decane, dodecane or mixtures thereof. Kerosine is particularly preferable. Suitable alkenes are for instance hexene, nonene, decene, dodecene or mixtures thereof. Suitable fatty acid esters are in particular alkyl stearates with alkyl groups having more than 2 C. atoms. Examples of fatty acid esters are ethyl stearate, butyl stearate, isopropyl stearate, ethyl palmitate and butyl linoleate. Particularly preferable are kerosine and butyl stearate. It is also possible to apply two or more of said organic compounds in the form of a mixture.

The liquid cation exchangers employed are preferably esters of inorganic acids and organic groups, which are preferably branched. The inorganic acids preferably are phosphoric acids, phosphorous acid, sulphuric acid and sulphurous acids. Phosphoric acid is preferred in particular. The organic residue groups applied according to the invention preferably are branched and/or non-branched alkyl or alkenyl groups with at least 4 C. atoms, preferably 4 to 20 C. atoms. The preferred liquid cation exchangers include di-2-ethylhexyl phosphoric acid esters, mono-2-ethylhexyl phosphoric acid esters, dinonylnaphthalene sulphonic acid esters or mixtures thereof. Preferred according to the invention is the mixture of di-2-ethylhexyl phosphoric acid ester and mono-2-ethylhexyl phosphoric acid ester. The mono-2-ethylhexyl phosphoric acid ester content of this mixture is preferably over 40 wt. %, more in particular over 80 wt. %, relative to the total amount of liquid cation exchanger.

Said liquid cation exchangers are preferably present in the extraction agent in an amount of 2 to 25 wt. %, relative to the amount of relatively long-chain organic compounds; particularly preferred are amounts of 5 to 20 wt. % of liquid cation exchanger and most preferred are amounts of 8 to 15 wt. % of liquid cation exchanger. According to the invention the extraction agent may contain other substances, including state-of-the-art extraction agents, besides the compounds mentioned here.

For the process according to the invention it is preferred to make use of a porous membrane which is wettable by either the aqueous mixture or by the extraction agent and has a pore density of 5 to 95%, more in particular a pore density of $\geq 30\%$, most preferably a pore density of $\geq 40\%$. The state-of-the-art porous membranes which are wettable by either the aqueous mixture or by the extraction agent can in principle be used for the process according to the invention. Membranes with a maximum pore density are preferred, particular preference being given to for instance hollow-fibre contactors.

Preferably, porous membranes with a pore size of $\leq 2\ \mu m$ are used for the process according to the invention, more in particular a pore size of $\leq 1\ \mu m$, more preferably a pore size of $\leq 0.5\ \mu m$, most preferably a pore size of $\leq 0.05\ \mu m$.

The process according to the invention is suitable in particular for the extraction of organic substances which contain at least one positively charged and/or chargeable nitrogenous group. Most preferably the process according to the invention can be used for the extraction of organic substances belonging to the group of aliphatic and/or aromatic amino acids and/or lactams, the salts, derivatives or di- or oligopeptides thereof or mixtures of these compounds.

The substances to be extracted include for instance L-amino acids or D-amino acids. In principle natural as well as non-natural amino acids can be extracted, such as all D- and L-forms of essential amino acids. Examples of extractable amino acids are L-phenylalanine, D-phenylalanine, L-tryptophane, D-tryptophane, L-tyrosine, D-tyrosine, D-p-hydroxyphenylglycine, D-phenylglycine, Di-hydroxyphenylalanine. Lactams can also be extracted by means of the process according to the invention, for instance β-lactams, caprolactam, penicillin G. Further, the process according to the invention can be used for the extraction of peptides, in particular di- or oligopeptides, for instance L-aspartyl-L-phenylalanine as a precursor molecule for the preparation of aspartame. Amino alcohols, for instance 1S, 2R-cis-(-)-aminoindanol, can also be extracted. Extraction according to the invention can also be applied for the recovery of amines or amides.

A preferred area of application of the process according to the invention is extraction from fermentation solutions, effluent flows and/or aqueous mixtures from chemical synthesis and/or degradation processes. In particular, the process according to the invention can be integrated into fermentation processes. The fermentation processes can be of an aerobic or an anaerobic nature and can be operated as batch, semi-continuous or continuous processes.

The invention further relates to a process which comprises the following steps:

a) the aqueous mixture is drawn from a reservoir,
b) led across a first porous membrane which is wettable by either t the aqueous mixture or by an extraction agent which contains at least partially relatively long-chain organic compounds and at least one liquid cation exchanger,
c) extracted with the extraction agent,
d) the aqueous retentate is returned to the reservoir,
e) the extracted organic substances are led across a second porous membrane which is wettable by either the aqueous mixture or by the extraction agent and
f) there re-extracted into an aqueous phase.

The process is preferably set up in such a way that in step d) the aqueous retentate is returned completely to the reservoir. It is also preferred for the pressure difference between the aqueous mixture and the extraction agent to lie between 0.1 and 10 bar, more in particular between 0.5 and 5 bar, most preferably between 2 and 3 bar.

In a particularly preferred embodiment of the process according to the invention the re-extraction can be effected with simultaneous concentration augmentation of the organic substances. Particular preference is given to re-extraction with simultaneous concentration augmentation of the organic substances.

A particularly preferred application area of the present invention is the extraction of substances from fermentation solutions. The fermentation processes can be of an aerobic or an anaerobic nature and can be operated as batch, semi-continuous or continuous processes. The process according to the invention is preferably set up in such a way that the extraction takes place continuously and simultaneously with a reaction that is proceeding in reservoir 1, for instance a fermentation reaction, i.e. in such a way that the extraction is integrated. As a special embodiment of the process according to the invention, the re-extraction of the organic substances into the aqueous phase can also take place as a process that is integrated relative to a reaction that proceeds in reservoir 1. The object of the invention is not restricted to such processes, however.

In the following, with reference to FIG. 1, the application of the process according to the invention is further elucidated on the basis of an integrated fermentation process:

Fermentation solution is continuously drawn from fermentor 1 and carried off via an ultrafiltration hollow-fibre module 2. In the hollow-fibre contactor 3 the organic substance to be separated from the fermentation solution is extracted into the extraction agent. According to the invention the extraction agent contains at least partially relatively long-chain organic compounds and at least one liquid cation exchanger. The aqueous retentate in the hollow-fibre contactor 3 is returned to fermentor 1 via a sterile filter 4. The extracted organic substance is passed through the hollow-fibre contactor 6 and, optionally with simultaneous concentration augmentation, re-extracted into an aqueous phase 7. According to a pre-formulated task the process can be so controlled for instance that the substance is crystallized out of this aqueous phase 7. If necessary, the ultrafiltration hollow-fibre module 2 and the sterile filter 4 can be dispensed with.

An essential advantage of the process according to the invention is the selective recovery of the desired organic substances with optionally simultaneous concentration augmentation. Concentrating of the organic substances according to the invention is effected together with the re-extraction into the aqueous phase. The special advantage of the process as described lies in the possibility to effect fermentation and extraction in an integrated process. This means that while a fermentation process is conducted in batch, semi-continuous or continuous mode, a continuously or simultaneously operated extraction process permits recovery of the desired organic substances. At the same time it is possible to return to the fermentation process the non-extracted portion of the fermentation solution (aqueous retentate). An end product inhibition of the cell-specific production is thus excluded. Moreover the extraction system employed is not toxic and due to a freely chosen pH value its environmental impact is very low. Moreover, it is in principle possible to supply the fermentation solution which still contains biomass into the extraction module directly and without previous cell separation, thus saving an additional process step.

By way of example the selective separation of L-phenyalanine from a model solution is described in detail below. The model solution represents a typical composition of a culture medium of a microbial fermentation process. By dissolving weighed portions of suitable salts in water the following concentrations of cations (Merck product) and amino acids (Fluka product) were set: as in Table 1.

For extraction of the L-phenylalanine 10 liters of model solution of the above-mentioned composition were pumped through the first hollow-fibre contactor (hollow-fibre module type Celgard Polypropylen, X30 240 ID from Hoechst Celanese AG) with a flow rate of 250 l/h, at pH 7 and a forerun temperature of 30° C. The pressure was 2.2 bar at the contactor inlet and 0.8 bar at the contactor outlet.

The extraction agent contained 10 vol. % di-2-ethylhexyl phosphoric acid ester (from Fluka), dissolved in kerosine (from Sigma Aldrich). The volume of extraction agent used was 7.5 liters. Counter currently to the aqueous phase of the model solution, the organic phase of the extraction agent was pumped round with a flow rate of 156 l/h through two hollow-fibre contactors in series. The inlet pressure of the first hollow-fibre contactor was 0.3 bar and the contactor outlet pressure was 0.2 bar. The inlet pressure of the second hollow-fibre contactor was 0.2 bar, the outlet pressure being 0.1 bar. The L-phenylalanine transferred into the organic phase of the extraction agent during the extraction was subsequently re-extracted into an aqueous phase. Six liters of aqueous phase were used, consisting of a $H_2SO_4$ solution (from Fluka) with a concentration of 1 mol/l and a pH value of 0. This aqueous phase was pumped through the second hollow-fibre contactor at a flow rate of 500 l/h, counter currently to the organic extraction agent phase. The inlet pressure of the hollow-fibre contactor was 1.2 bar, the outlet pressure being 0.5 bar.

The selectivity of the extraction with respect to the cations and amino acids listed in table 1 was 95% or more. It proved to be possible to increase the concentration of the L-phenylalanine in the aqueous phase by 20% up to a range of 400 to 500% compared with the quantity applied in the model solution.

A further positive effect of the process according to the invention is that due to the addition of liquid cation exchanger to the model solution, the reaction in reservoir 1 yields at least 40% more organic substance than in the situation with the model solution without liquid cation exchanger.

TABLE 1

| Cation | mg/l | mmol/l | Amino Acid | [mmol/l] | [g/l] |
|---|---|---|---|---|---|
| Na | 2990.00 | 130.56789 | Asp | 1 | 0.13212 |
| Mg | 33.00 | 1.35802 | Glu | 0.1 | 0.014714 |
| Al | 0.62 | 0.00002 | Asn | 0.047 | 0.00620964 |
| Si | 9.20 | 0.00033 | Ser | 0.045 | 0.0047295 |
| K | 1067.00 | 0.02729 | Gln | 0 | 0 |

TABLE 1-continued

| Cation | mg/l | mmol/l | Amino Acid | [mmol/l] | [g/l] |
|---|---|---|---|---|---|
| Mn | 0.14 | 0.00255 | His | 0.045 | 0.0069822 |
| Fe | 1.00 | 0.01790 | Gly | 0.97 | 0.0728179 |
| Ni | 0.35 | 0.00596 | Thr | 0.106 | 0.01262672 |
| Cu | 0.36 | 0.00567 | Arg | 0.135 | 0.02351835 |
| Zn | 0.12 | 0.00184 | Ala | 2.49 | 0.221859 |
| Mo | 1.25 | 0.01303 | Tyr | 0.47 | 0.085164 |
|  |  |  | Trp | 0 | 0 |
| $NH_4$ | 3330.00 | 185.00000 | Met | 9.7035 | 1.44795627 |
|  |  |  | Val | 0 | 0 |
|  |  |  | Phe | 118.719 | 19.6123788 |
|  |  |  | Ile | 0.196 | 0.02571128 |
|  |  |  | Leu | 0.643 | 0.08434874 |
|  |  |  | Lys | 0.357 | 0.05218983 |

What is claimed is:

1. Process for separating from an aqueous mixture one or more organic substances containing at least one positively charged and/or chargeable nitrogenous group by extracting the at least one nitrogenous group-containing organic substance via at least one porous membrane, comprising contacting one surface of the porous membrane with the aqueous mixture and contacting another surface of the porous membrane with an extraction agent which comprises at least one relatively long-chain organic compound and at least one liquid cation exchanger, wherein said at least one porous membrane is wettable by either the aqueous mixture or by the extraction agent, whereby the at least one nitrogenous group-containing organic substance is separated from the aqueous mixture.

2. Process according to claim 1, which further comprises re-extracting one or more nitrogenous group-containing organic substances from the extraction agent into an aqueous phase.

3. Process according to claim 1, wherein the relatively long-chain organic compound comprises at least one organic compound having 6 to 20 C atoms.

4. Process according to claim 1, wherein the relatively long-chain organic compound comprises at least one of alkanes, alkenes or fatty acid esters.

5. Process according to claim 1, wherein at least one said liquid cation exchanger comprises an ester of an inorganic acid and an organic residue group.

6. Process according to claim 1, wherein at least one said liquid cation exchanger comprises at least one ester of phosphoric acid, phosphorous acid, sulphuric acid or sulphurous acid.

7. Process according to claim 1, wherein at least one said liquid cation exchanger comprises at least one of di-2-ethylhexyl phosphoric acid esters, mono-2-ethylhexyl phosphoric acid esters, dinonylnaphthalene sulphonic acid esters or mixtures thereof.

8. Process according to claim 1, wherein at least one said liquid cation exchanger is employed in an amount of 2 to 25 wt. %, relative to the amount of relatively long-chain organic compound.

9. Process according to claim 1, wherein one or more said nitrogenous group-containing organic substances comprise one or more of aliphatic and/or aromatic amino acids and/or lactams, the salts, derivatives or di- or oligopeptides thereof or mixtures of these compounds.

10. Process according to claim 1, wherein a porous membrane having a pore density of 5 to 95% is employed.

11. Process according to claim 1, wherein a porous membrane having a pore density of at least 40%, is employed.

12. Process of claim 1, wherein a hollow-fibre contactor is employed as a porous membrane.

13. Process according to claim 1, wherein said aqueous mixture comprises at least one of fermentation solutions, effluent flows and/or aqueous mixtures from chemical synthesis and/or degradation processes.

14. Process according to claim 1, wherein the at least one relatively long-chain organic compound comprises at least one organic compound having from 12 to 18 carbon atoms.

15. Process according to claim 1, wherein said at least one liquid cation exchanger is employed in an amount of 5 to 20 wt. %, relative to the amount of relatively long-chain organic compound.

16. Process for separating from an aqueous mixture one or more organic substances containing at least one positively charged and/or chargeable nitrogenous group by extraction via at least one porous membrane, comprising:

a) drawing the aqueous mixture from a reservoir, b) transporting the aqueous mixture along a first surface of a first porous membrane, said membrane is wettable by either the aqueous mixture or by an extraction agent which comprises at least one relatively long-chain organic compound and at least one liquid cation exchanger, and contacting a second surface of the first porous membrane with said extraction agent:

c) extracting the one or more nitrogenous group-containing organic substances from the aqueous solution with the extraction agent, d) returning aqueous retentate to the reservoir, e) transporting the extractant containing the one or more nitrogenous-containing organic substances along a first surface of a second porous membrane which is wettable by either the aqueous mixture or by the extraction agent, and f) re-extracting the extracted one or more nitrogenous group-containing organic substances into an aqueous phase contacting the second porous membrane.

17. Process according to claim 16, wherein in stage d) the aqueous retentate is completely returned to said reservoir.

18. Process according to claim 16, wherein the pressure difference between the aqueous mixture and the extraction agent lies between 0.1 and 10 bar.

19. Process according to claim 16, wherein the re-extraction is effected with simultaneous concentration augmentation of the one or more nitrogenous group-containing organic substances.

20. Process according to claim 16, wherein a reaction is proceeding in said reservoir and the extraction takes place continuously and simultaneously with said reaction.

* * * * *